United States Patent
Zhang et al.

(10) Patent No.: US 12,376,932 B2
(45) Date of Patent: *Aug. 5, 2025

(54) STERILE DRAPING OF ROBOTIC ARMS

(71) Applicant: GLOBUS MEDICAL, INC., Audubon, PA (US)

(72) Inventors: Kevin Zhang, Medford, MA (US); Norbert Johnson, North Andover, MA (US); Mir Hussain, Downingtown, PA (US); James Cascarano, Cambridge, MA (US); Justin Larson, Reading, MA (US); James Yau, Methuen, MA (US); Robert LeBoeuf, II, Salem, NH (US); Michael Norcia, North Andover, MA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/470,904

(22) Filed: Sep. 20, 2023

(65) Prior Publication Data

US 2024/0008945 A1 Jan. 11, 2024

Related U.S. Application Data

(63) Continuation of application No. 16/936,698, filed on Jul. 23, 2020, now Pat. No. 11,793,588.

(51) Int. Cl.
*A61B 46/10* (2016.01)
*A61B 34/30* (2016.01)

(52) U.S. Cl.
CPC .............. *A61B 46/10* (2016.02); *A61B 34/30* (2016.02)

(58) Field of Classification Search
USPC ............................................................ 606/1
See application file for complete search history.

(56) References Cited

U.S. PATENT DOCUMENTS

| | | |
|---|---|---|
| 4,150,293 A | 4/1979 | Franke |
| 5,246,010 A | 9/1993 | Gazzara et al. |
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |

(Continued)

OTHER PUBLICATIONS

US 8,231,638 B2, 07/2012, Swarup et al. (withdrawn)

*Primary Examiner* — Jennifer Pitrak McDonald
*Assistant Examiner* — Michael T. Holtzclaw (57) ABSTRACT

A drape covers robotic equipment in a medical environment to maintain sterility. The robotic equipment has an arm with an end surface which attaches to a tool, such as an active end effector. The drape has an extended drape portion that covers the arm, and a shaped drape portion that covers the end of the arm where the arm is clamped to the tool. The drape is clamped inside the clamp, and where the clamping occurs, the drape has a band of material that is reinforced by being thickened or by including a different material. The shape of the band corresponds to the portion of the arm that is clamped by the clamp.

20 Claims, 4 Drawing Sheets

(56) References Cited

U.S. PATENT DOCUMENTS

| | | |
|---|---|---|
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |

(56) References Cited

U.S. PATENT DOCUMENTS

| | | |
|---|---|---|
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Wllliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |

(56) References Cited

U.S. PATENT DOCUMENTS

| | | |
|---|---|---|
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |

(56) References Cited

U.S. PATENT DOCUMENTS

| | | |
|---|---|---|
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0292707 A1* | 11/2010 | Ortmaier ............... B25J 19/0075 606/130 |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |

(56) References Cited

U.S. PATENT DOCUMENTS

| | | |
|---|---|---|
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0202009 A1* | 7/2015 | Nussbaumer .......... A61B 46/10 128/856 |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2019/0099232 A1* | 4/2019 | Soto .................. A61B 90/39 |
| 2019/0290379 A1* | 9/2019 | Flatt .................. A61B 34/30 |
| 2020/0170724 A1* | 6/2020 | Flatt .................. A61B 46/10 |

\* cited by examiner

STERILE DRAPING OF ROBOTIC ARMS

CROSS-REFERENCE TO RELATED APPLICATION(S)

The present application is a continuation of U.S. patent application Ser. No. 16/936,698, filed on Jul. 23, 2020 (published as U.S. Pat. Pub. No. 2022-0022990), the entire content of which is incorporated herein by reference in its entirety for all purposes.

FIELD OF THE INVENTION

This invention relates to draping robotic arms for sterility in an operating theatre, and more particularly to protecting a drape that is clamped within the robotic arm from becoming torn.

BACKGROUND OF THE INVENTION

Position recognition systems are used to determine the position of and track a particular object in 3-dimensions (3D). In robot assisted surgeries, for example, certain objects, such as surgical instruments, need to be tracked with a high degree of precision as the instrument is being positioned and moved by a robot or by a physician, for example.

With either active or passive tracking sensors, the system geometrically resolves the 3-dimensional position of active and/or passive sensors based on information from or with respect to one or more of the infrared cameras, digital signals, known locations of the active or passive sensors, distance, the time it took to receive the responsive signals, other known variables, or a combination thereof.

In order to accomplish this, power transfer and data communications must be carried out between a robotics base station locator (GPS), and a replaceable end effector tool. However, a surgical drape must be interposed between the base and a tool, precluding a direct electrical connection.

To transfer power and enable one-way data transfer, the ExcelsiusGPS system, for example, uses a pair of wireless charging coils, one being positioned in a moveable arm attached to the base, and the other in the tool. Power is transferred by induction through both the drape material and an air gap from the arm to the tool. Data signals are sent from the tool to the base by changing the load placed upon the coils during power transfer for predetermined time periods. The specific time period of change is observed by the base and correlated to a particular command or status.

To maintain a sterile field in the operating room, to avoid a requirement of sterilizing an entire robotics device, a drape is pulled over the robotic arm and is pulled against the palm assembly. A clamp that is attached to an active end effector is clamped onto the arm, with the drape trapped in the clamp. Movement of the arm and pulling on the drape after clamping increases the tension on the drape, particularly at the point of clamping, to an extent where the drape is susceptible to being torn. Clamping the drape also creates stress concentrations, and the drape may become torn though repeated clamping, particularly when large forces are transmitted through the drape within the clamp interface.

SUMMARY OF THE INVENTION

In an embodiment of the disclosure, a drape for covering robotic equipment in a medical environment, the robotic equipment having an arm and an arm portion with an end surface and a tool which attaches to the arm portion with a clamp, the drape comprises an extended drape portion of a first material sized to cover the arm; and a shaped drape portion sized to cover the arm end surface, the shaped drape portion defined by a band of second material that is reinforced relative to the first material, the band shaped to correspond to the portion of the arm that is clamped by the clamp; whereby the clamp clamps the band when the clamp clamps the arm portion to the tool.

In variations thereof, the second material is reinforced by being the same type of material as the first material, and which is thicker than the first material; the second material is reinforced by being a different type of material that is more resistant to physical deformation than the first material; the band has at least one indexing region that is shaped to mate with an indexing region of the clamp; the second material is a dielectric material; the band is a thermoplastic polyurethane; and/or the band includes a first band portion sized to be pressed by the clamp during clamping, and a second band portion extending away from the first portion to thereby provide strain relief at a transition from the shaped drape portion to the extended drape portion.

In further variations thereof, the second band portion is tapered; the shaped drape portion is formed separately from the extended drape portion and affixed to the extended drape portion; and/or the clamp is a v-band type, the arm portion including a flange squeezed by a v-band of the v-band clamp, the band having a loop shape sized to cover the squeezed portion of the flange; the arm portion includes a flange squeezed by the clamp, the flange having the band having a loop shape sized to cover the squeezed portion of the flange In other variations thereof, the drape further includes a plurality of electrically conductive contacts within the shaped drape portion, the electrically conductive contacts operative to conduct electricity from a first side of the shaped drape portion to a second side of the shaped drape portion opposite to the first side; the electrically conductive contacts are integrally formed within the second material by 3D printing; the drape further includes a plurality of capacitive plates affixed to, positioned within, and on a first side of the shaped drape portion; and/or the shaped drape portion including electrically conductive contacts.

In accordance with another embodiment of the disclosure, a drape for covering robotic equipment in a medical environment, the robotic equipment having an arm and an arm portion with an end surface with a flange having an indexing shape and a tool which attaches to the arm portion with a clamp, the clamp including an indexing shape corresponding to the indexing shape of the flange, the drape comprises an extended drape portion of a first material sized to cover the arm; and a shaped drape portion sized to cover the arm end surface, the shaped drape portion defined by a band of second material that is at least one of thicker than the first material and including a different material than the first material whereby the second material is reinforced relative to the first material, the band shaped to correspond to the flange and having an indexing shape which corresponds to the indexing shape of the flange; whereby the clamp clamps the band when the clamp clamps the arm portion to the tool.

In a variation thereof, the drape further includes a plurality of electrically conductive contacts within the shaped drape portion, the electrically conductive contacts operative to conduct electricity from a first side of the shaped drape portion to a second side of the shaped drape portion opposite to the first side.

Further in accordance with the disclosure, a method of draping robotic equipment in a medical environment for sterility, the robotic equipment having an arm and an arm portion with an end surface and a tool which attaches to the arm portion with a clamp, comprises providing a drape having: an extended drape portion of a first material sized to cover the arm; and a shaped drape portion sized to cover the arm end surface, the shaped drape portion defined by a band of second material that is reinforced relative to the first material, the band shaped to correspond to the portion of the arm that is clamped by the clamp; whereby the clamp clamps the band when the clamp clamps the arm portion to the tool.

In variations thereof, the method further includes providing an intermediate coupling which is sized and dimensioned on a first end to be clampable to the arm with the drape passing between the intermediate coupling and the arm, the intermediate coupling having a second end sized and dimensioned to be clampable to the tool; whereby the tool can be attached to the robotic equipment without a requirement of unclamping the drape; and/or the clamp has an indexing region, the band having an indexing region corresponding to the indexing region of the clamp.

BRIEF DESCRIPTION OF THE DRAWINGS

A more complete understanding of the disclosure, and the attendant advantages and features thereof, will be more readily understood by reference to the following detailed description when considered in conjunction with the accompanying drawings, in which.

DETAILED DESCRIPTION OF THE INVENTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). Headings are provided for the convenience of the reader, and are not intended to be limiting in any way.

A problem with prior art surgical drapes when covering robotic devices is that power transfer and communication must be accomplished through the drape in order to maintain a sterile field. However, a direct electrical connection is the most efficient type of connection for power transfer and communication, and this is not possible with a prior art drape. The disclosure provides solutions which maintain sterility while also providing efficient power transfer and communication data exchange between a draped robotics base (e.g. GPS) and an attached tool (e.g. an active end effector) of a robotic device.

Figures 1, 2, 3, 4, 5:
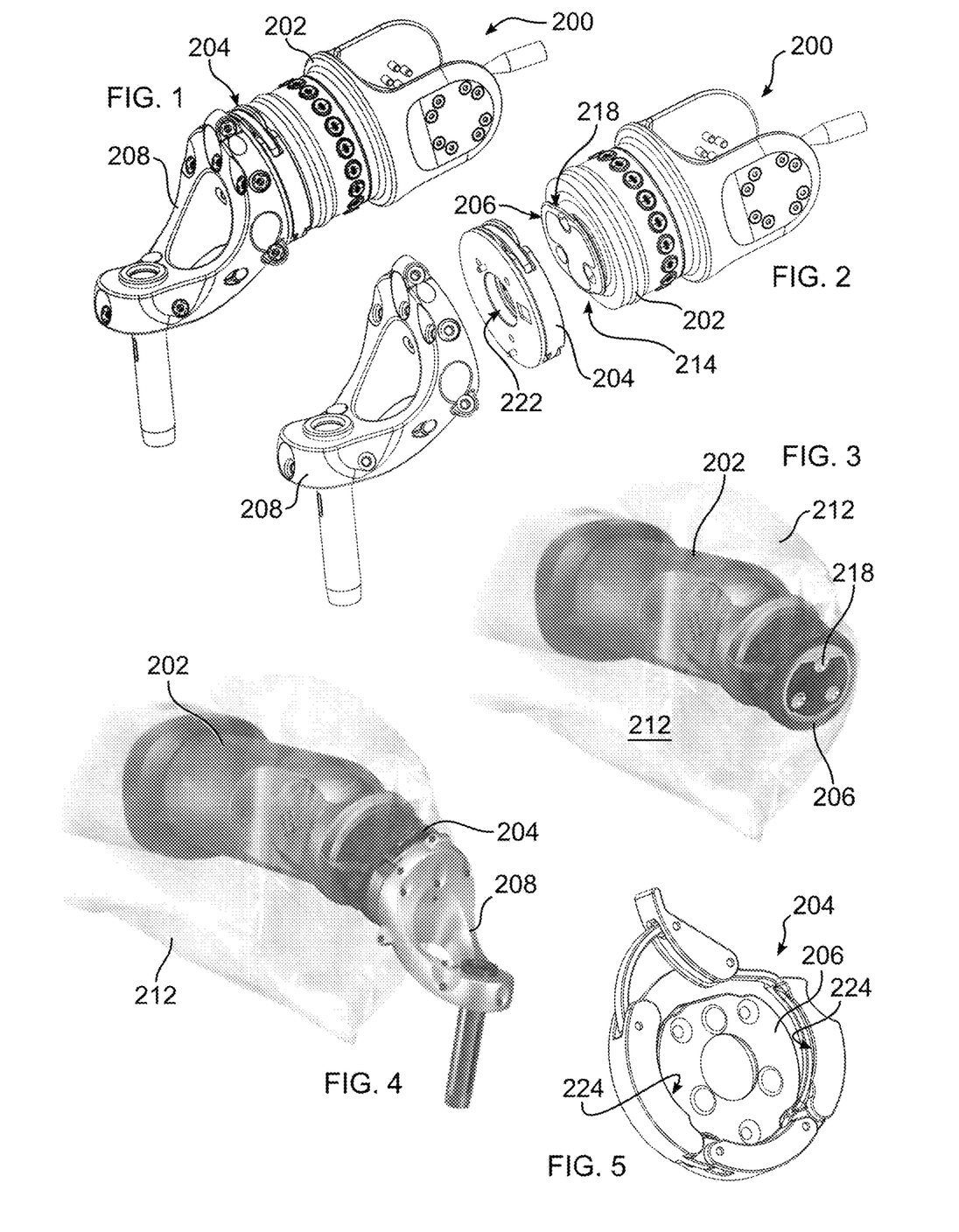
FIG. 1 depicts a robotics system, including an arm/palm unit, a clamp, and a tool/AEE.
FIG. 2 depicts the robotics system of FIG. 1 where components are separated.
FIG. 3 depicts the robotics system of FIG. 1, the arm covered by a PRIOR ART drape.
FIG. 4 depicts the robotics system and drape of FIG. 3, the clamp and tool assembled over the drape.
FIG. 5 depicts the clamp of FIG. 1, separated from the tool, and in an opened configuration.

With reference to FIGS. 1-4, a robotic surgical aid system 200, such as the ExcelsiusGPS, includes a connection between a "GPS" arm or other type of robotic arm 202 and an active end-effector ("AEE") tool 208, where arm 202 is draped for sterility during surgical procedures. In particular, a sterile drape 212 is placed around and over the end of the arm before tool 208 is attached to arm 202. Tool 208 is secured to arm 202 with a clamp 204, such as a V-band clamp as shown, clamp 204 passing over and squeezing together mating flanges 206, 210 of arm 202 and tool 208. During clamping, drape 212 is also clamped because it drapes over flange 206 of arm 202. With reference to FIGS. 3-4, depicting a prior art drape, it may be seen that as a result of clamping, drape 212 is forcefully pinched. This can lead to prior art drapes 212 becoming worn or torn though repeated clamping, which can result in increased microbial exposure to the patient, and which requires replacement of the drape.

More particularly, as can be seen in FIGS. 3-4, drape 212 is pulled over arm 202 and is pulled against the palm assembly, or end face 214 of arm 202. With no end-effector 208 attached, drape 212 can slide or shift with respect to arm 202, and there is a low probability of shear or tensile forces tearing drape 212. With tool 208 attached, as in FIG. 4, some of drape 212 will be locked in place by the clamping force of clamp 204. Movement of the arm and pulling on drape 212 after clamping increases the tension on the drape, particularly at the point of clamping, to an extent where the drape is susceptible to being torn. Clamping drape 212 also creates stress concentrations, and the drape may become torn though repeated clamping, particularly when large forces are transmitted through the drape within the clamp interface. The disclosure provides a drape 102 which addresses these and other problems.

Drape

With reference to FIGS. 6-16, a device 100 in accordance with the disclosure includes a drape 102, which fulfills the functions of drape 212, and which is provided with a band 104 which is one or more of thickened, replaced with an alternative material, or reinforced by being supplemented with additional material which can be the same or different from the material of a remainder of the drape 102. Reinforcement may alternatively be provided by band 104 being thicker or by being fabricated with an additional material, with the result that band 104 is more resistant than a remainder of drape 102 to abrasion, tearing, crushing, bunching, skewing, stretching, or other physical deformation as a result of being under a clamping portion 224 of clamp 104 while clamp 104 is closed or clamped. Band 104 is provided to prevent tearing or other damage to drape 102 in the area of clamping, which could adversely affect an ability of a drape to maintain a sterile field. A remainder of drape 102, which is not subject to clamping forces, can be relatively thinner, weaker, less expensive, and/or easier to manufacture than band 104, while still able to maintain sterility without a need for strengthening or reinforcement.

Band 104 is defined in shape and size by an area of drape 102 which would pass between clamp 204 and flange 206 of arm 202, whether the clamp is a V-band clamp as shown in the figures, or some other clamp style. Band 104 can be larger than the clamping area to provide additional strain relief. The extended or larger portion can be tapered for more effective strain relief. Band 104 reduces the possibility of chafing, tearing, and wear of drape 102 in the area of the clamp, particularly during movements of arm 202 and tool 208 during a surgical procedure, or if drape 102 is pulled.

Figures 6, 7, 8, 9:
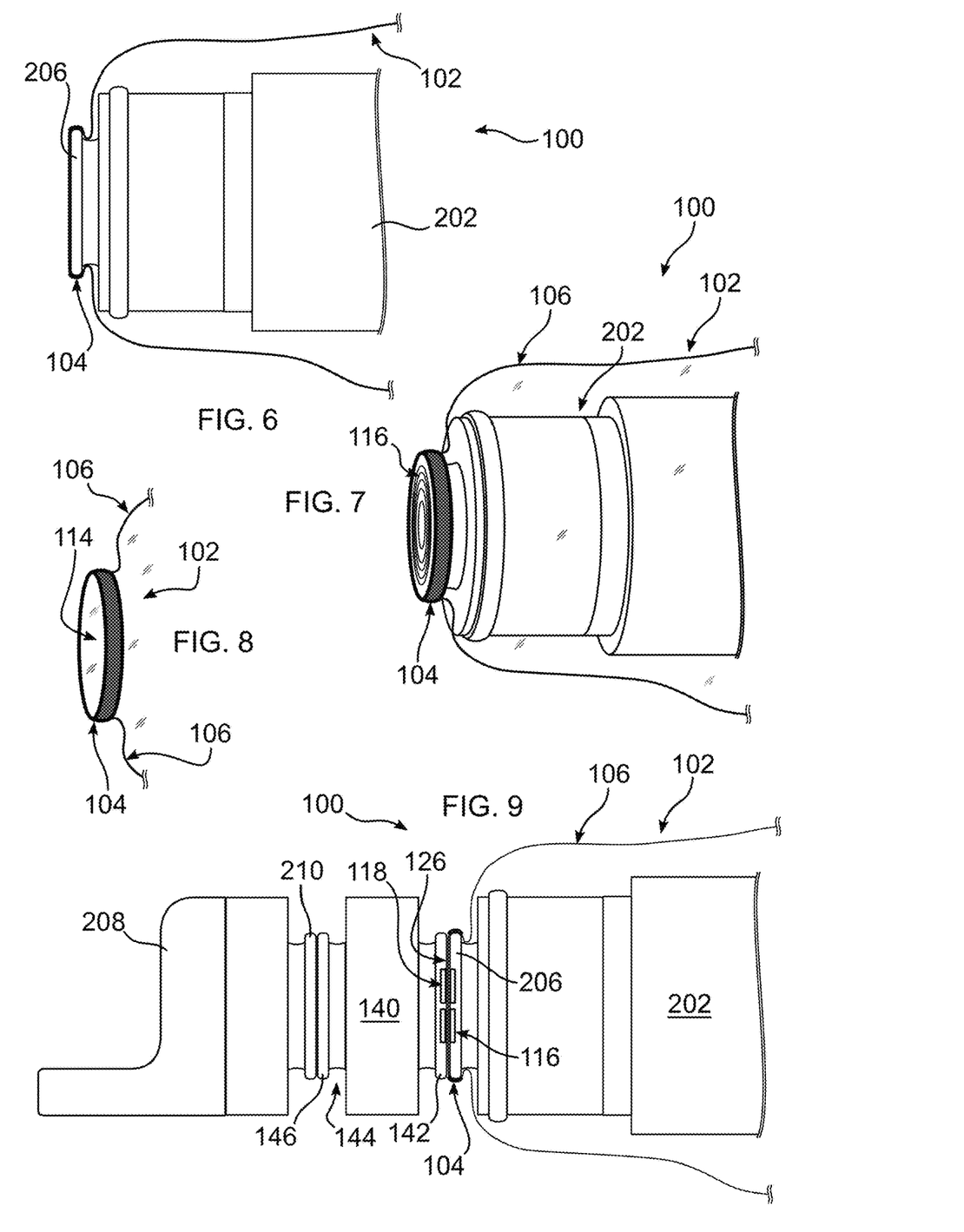
FIG. 6 depicts a robotics arm covered by a drape of the disclosure, the drape including a reinforcing band.
FIG. 7 depicts the robotics arm and drape of FIG. 6, capacitive plates of the disclosure positioned upon the arm and visible through a portion of the drape inside of the band.
FIG. 8 depicts the drape of FIG. 6, removed from the arm.
FIG. 9 depicts the drape and arm of FIG. 6, with capacitive plates shown in cross-section, and further depicting an intermediate coupling interposed between the arm and a tool.

As shown in FIG. 8, it may be seen that drape 102 defines a general draping portion 106 which extends away from band 104 to cover arm 202 and other components, and a coupling region 114 which extends away from and inside band 104 to cover end face 214 of arm 202, which in the example shown is a palm assembly. Coupling region 114 therefore lies between arm 202 and tool 208, in use. As detailed elsewhere herein, it can be advantageous for drape 102 to be thin in coupling region 114. FIG. 7 depicts drape 102 positioned over end face 214. As drape 102 can be transparent, as depicted in FIG. 6, end face 214 and conductive plates 116 can be visible through drape 102.

It is important that material of band 104 be both durable and sufficiently thin to allow tool 208 to properly clamp and without resulting in extra space that could possibly introduce play between the palm/arm 202 and tool 208.

Band 104 can be formed by adding material to one or both sides of drape 102. The additional material can be highly resistant to abrasion, or can be partially abraded, while still protecting the underlying or inner layer of drape material. Band 104 can be formed with a resilient material which can absorb and distribute clamping force. A resilient material additionally has the advantage of providing strain relief if extending outside of the clamped area in either or both directions. Alternatively, a relatively hard or non-resilient material can be used, such as a metallic foil, as the abrasion from clamping would be applied to the hard material, and not the underlying drape. The hard material can be thin, particularly where it extends outside of the clamped area, in order to retain some of the properties of a resilient material with respect to strain relief.

Band 104 can alternatively be inserted into a cut out region of drape 102, whereby an interior panel is attached to one side of band 104 to cover end face 214, and an exterior panel extends away from band 104 to cover arm 202. The interior and exterior panels can be attached to band 104 by any known means, including adhesion, ultrasonic welding, crimping, or clamping, as examples.

In an embodiment, drape 102 is molded or otherwise formed to have band 104 in a predetermined location. Band 104 can additionally or alternatively be formed by welding, adhering, bonding, or otherwise affixing a reinforcing material, such as an abrasion or crush resistant material, over one or both sides of, or throughout, an area of drape 102 which is positioned upon drape 102 to cover end face 214 of arm 202 when drape 102 is in use, or to cover the portion of drape 102 which will lie within the clamped area of the clamp. The method of affixing should not result in openings in drape 102 which could compromise the sterile field properties of drape 102. The reinforcing material can be any material that can bond to, attach to, or be formed from the material of draping portion 106 and coupling region 114, e.g. the material of drape 102 generally, and which is compatible with any other requirements of the operating theatre. Examples include a plastic material, for example a thermoplastic elastomer or thermoplastic polyurethane, a rubber or rubberized material, such as vulcanized rubber, polyvinylchloride (PVC), as non-limiting examples. While the material of band 104 can be resilient, it can be more rigid than material of drape 102, which helps to prevent bunching, crumpling, or other deformation of band 104 during clamping, which could lead to tearing. If drape 102 is to function in a capacitive conduction configuration, as described herein, a selection of material is additionally influenced by a desired dielectric constant of the material.

The material for band 104 is advantageously sterilizable using ethylene oxide (EtO) or gamma radiation. Thermoplastic polyurethane (TPU) has been noted to have no significant negative effects from sterilization with EtO. It should be considered that some materials can become brittle when exposed to gamma radiation, in which case a material which is sterilizable in both manners is advantageous.

FIGS. 6-9 illustrate band 104 formed as a reinforced band 104 wrapping around flange 206. In this manner, clamping force is only applied to the band 104, and not to the rest of the drape material 106. When clamped, there is no relative motion between arm 202, tool 208, band 104, and a GPS portion of the robotics system. Clamping additionally enforces alignment and contact of any power transfer elements in the area of band 104, as discussed in greater detail elsewhere herein.

With reference to FIG. 9, flange 206 can be provided with a periphery that is non-uniform in shape, and which has indexing elements 218, for example flattened sides on an otherwise circular peripheral shape, as can be seen in FIG. 2. This can be used to guide indexing or relative alignment between arm 202 and clamp 204. In the embodiment shown, clamp 204 is affixed to tool 208 by bolts or other fastener, resulting in appropriate indexing of clamp 204 relative to tool 208. However, where tool 208 is provided as a separate part, it can be provided with a flange having an indexing element 218. Clamp 204 has internal surfaces which mate with indexing element 218, whereby clamping cannot be accomplished until a proper orientation of flange 206 and clamp 204 is attained. During clamping, further alignment and indexing is carried out as a clamping force is applied to the clamped parts.

Figures 10, 11:
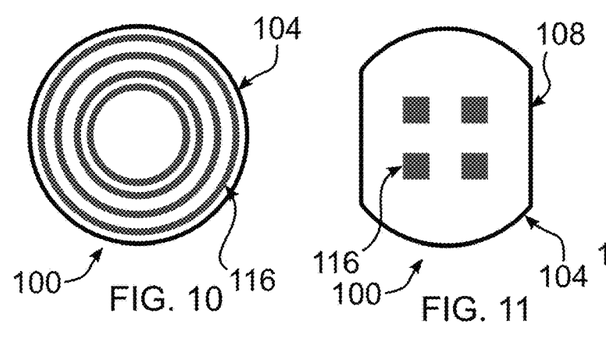
FIG. 10 depicts a pattern of capacitive plates in accordance with the disclosure.
FIG. 11 depicts an alternative pattern of capacitive plates in accordance with the disclosure, and an indexing shape.
Figure 12:
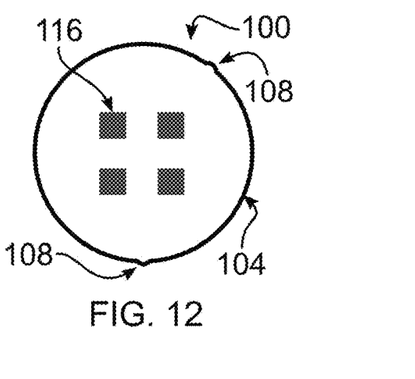
FIG. 12 depicts a further alternative pattern of capacitive plates in accordance with the disclosure, and indexing elements.

Accordingly, with reference to FIGS. 11-12, band 104 can be provided with a shape which includes indexing elements 108 which correspond to mating indexing elements 218 of flange 206. In this manner, band 104 can only be inserted over flange 206 in the correct orientation. FIG. 12 depicts an alternative indexing element 108, 218 shape, although other shapes are possible.

Herein, in embodiments where clamp 204 is affixed to tool 208, a portion of tool 208 can extend through or into an opening 222 (FIG. 2) in clamp 204, which portion includes electrical contacts or conductive plates 218. Alternatively, contacts or conductive plates 218 can be affixed to clamp 204 (FIGS. 17-19), and wires (not shown) can extend from these into tool 208.

Figures 18, 19, 20:
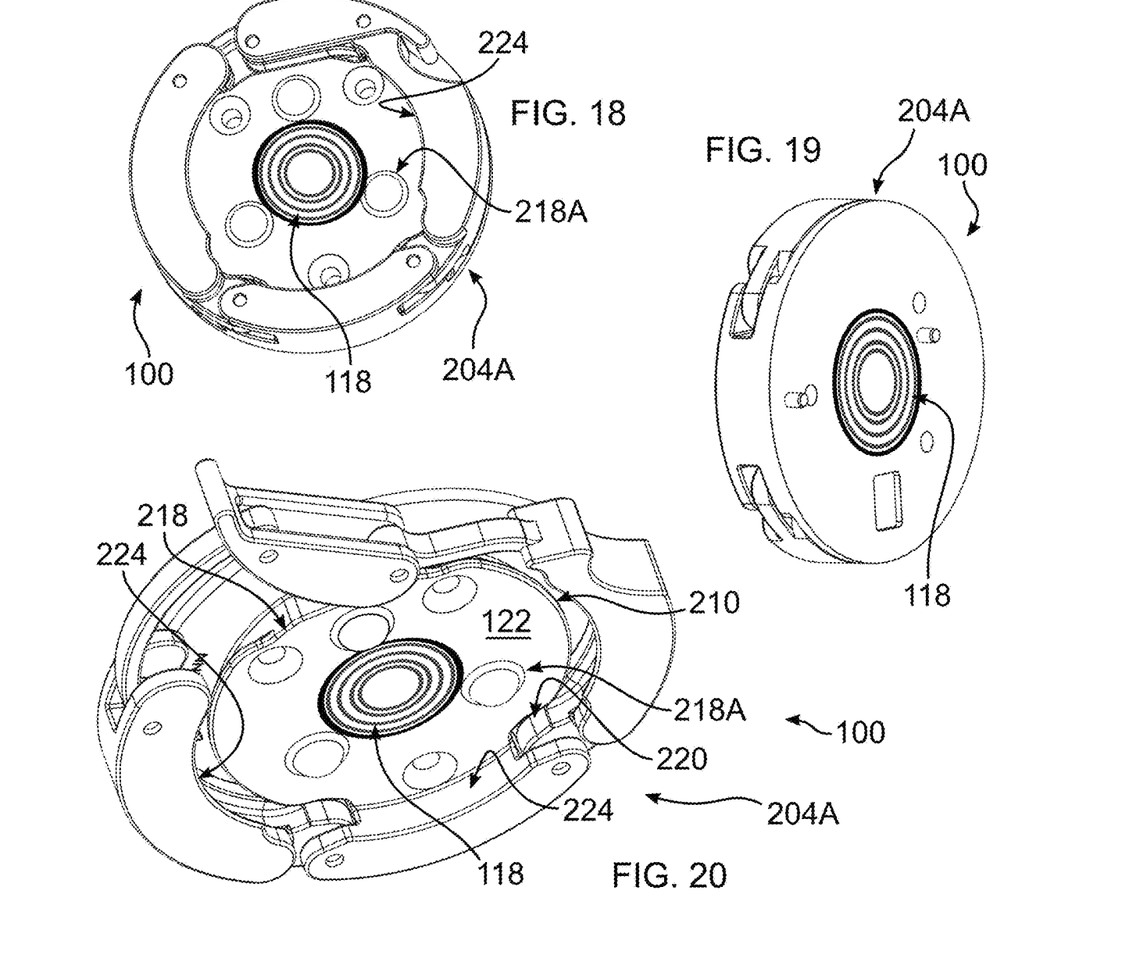
FIGS. 18-20 depicts a clamp of the disclosure including a plurality of capacitive plates.

FIG. 20 illustrates an alternative method of indexing arm 202 and clamp 104/tool 208 in accordance with the disclosure. An indexing element 218A has the form of several raised shapes on a plate within clamp 204. Alternatively, the raised shapes can be provided on an endplate of flange 210 of tool 208, where tool 208 is not affixed to clamp 204. Mating depressions (not shown) can be formed in end face 214 of arm 202. The indexing elements can be placed in an irregular pattern enforcing a unique alignment of arm 202 and tool 208.

To affix drape 102 to the robot, the user first places band 104 area over flange 106 at end face 214 at the end of the GPS arm 202. If flange 106 and band 104 have indexing elements 218, 108, respectively, these are aligned by rotating either drape 102 or arm 202 into alignment. In the embodiment shown, flange 210 is affixed to clamp 204 and tool 108, so alignment can be carried out using only indexing elements 218. Other indexing elements can be provided within clamp 204, such as indexing elements 220, shown in FIG. 20. If clamp 204 were not affixed to tool 208, indexing elements 218 of flange 210 would be aligned within clamp 204 to be aligned with indexing elements 218 of flange 206 and any indexing elements of clamp 204. Once all components are aligned, clamp 204 can be tightened over band 104. Electrical To perform power and data transfer, the ExcelsiusGPS, for example, uses a pair of wireless charging coils (not shown) for power transfer and communication. One coil is positioned in arm 202 adjacent flange 206, and the other coil is positioned in tool 208 proximate flange 210, whereby power can be transferred by induction through both the drape material and an air gap between tool 208 and arm 202.

In the ExcelsiusGPS, communication is unidirectional, from tool 208 to arm 202, and is achieved by modulating the power level (load) of the charging coil of the tool. For instance, tool 208 sends data signals by changing the load to define specific time periods, each indicating a different status condition. These periods include, for example, a period of 66 ms to indicate 'end-effector connected', 90 ms for 'tool inserted', and 110 ms for 'error state'.

The aforedescribed data and power transfer methods adequately meet existing requirements, but it is desired to be able to bidirectionally transfer information at a higher bandwidth, and with increased power transfer efficiency, each of which are addressed by the instant disclosure.

Further, while the aforedescribed bandwidth and power efficiency challenges are described in the context of the ExcelsiusGPS, it is attendant to other models and brands of robotic arm configurations, and electrical equipment that is not robotic but includes similar requirements with respect to draping. This disclosure is intended to address such problem in any configuration where a tool portion inside a sterile field must be mechanically attached to another tool portion that is intended to remain outside the sterile field, and whether or not there is a requirement to transfer an electrical signal through a drape.

More particularly, in accordance with the disclosure, electronic communication and optionally power are transmitted through drape 102 using capacitive coupling. Coupling region 114 of drape 102 functions as a dielectric, separating capacitive elements disposed upon either side of coupling region 114 that are associated with tool 208 and arm 202. In this manner, communication and energy transfer take place through drape 102, without requiring an opening in drape 102, preserving the sterile field created by drape 102.

Similar in some respects to electromagnetic induction, capacitively coupled signaling uses metallic plates and an interposed dielectric. In accordance with the disclosure, drape 102 functions as the dielectric, and an electrical connection is thereby established in order to accomplish the transmission of data. By nature, capacitive connections provide the ability to transfer data faster than electromagnetic induction. In addition, increasing the number of metal plate pairs can enable a corresponding increase in data or power throughput. Each plate pair enables a separate bidirectional communication path, and individually or collectively, the pairs eliminate a requirement that the end-effector modulate an inductive load in order to communicate when using magnetic power induction. In one embodiment, communication is provided by capacitive coupling, and power transfer is accomplished by induction and/or a wired connection to tool 208.

More particularly, with reference to FIGS. 10-12, a plurality of capacitive plates 116 are positioned on or near flange 206 upon a surface of end face 214. A matching plurality of capacitive plates 118 are positioned adjacent flange 210 either (a) on an end surface 122 of clamp 204A (FIG. 20), (b) on an end surface 124 of tool 208 (FIG. 16), or (c) an end surface 126 of an intermediate coupling 140 (FIG. 9, as detailed elsewhere herein). Drape 102 passes between plates 116, 118 when their respective components are clamped together. With respect to surface 122/124/126, either or both of plates 116, 118 can be positioned to extend above, be even with, or be below the surface, determined by optimal transmission efficiency and a desired component fitment. The number of plate 116/118 pairs is selected based upon considerations including the number of desired data streams and total desired bandwidth, the amount of available power, and a desire for redundant data or power streams, as examples.

Figure 13:
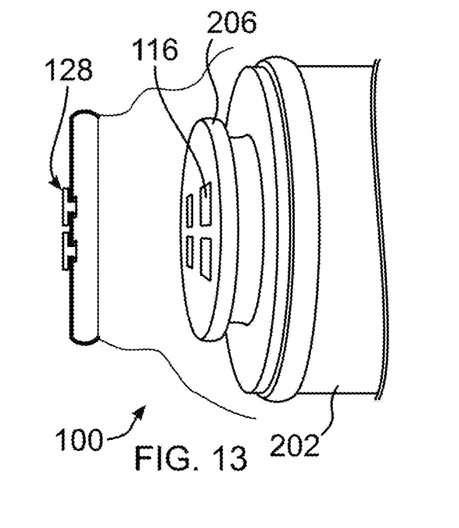
FIG. 13 depicts a robotic arm of the disclosure including a cross-section of electrical contacts, and a drape of the disclosure including a reinforced band and electrical contacts which pass through the drape and mate with electrical contacts of the arm.
Figure 14:
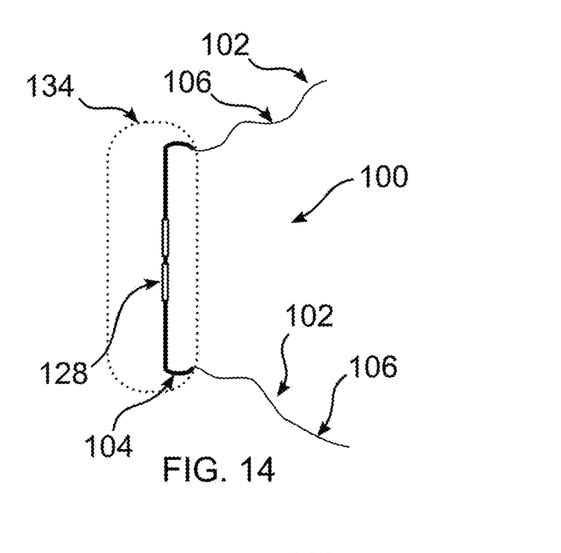
FIG. 14 depicts the drape of FIG. 13, with contacts which are integrated into the drape, the dashed line indicating a replaceable portion of a drape.
Figure 15:
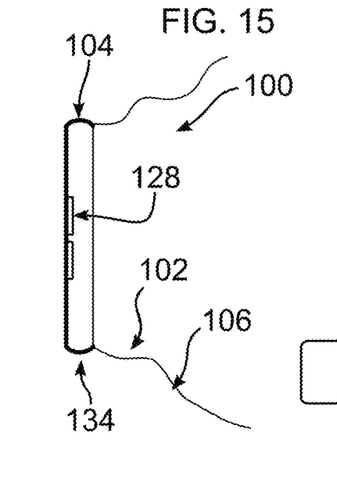
FIG. 15 depicts the drape of FIG. 13, with contacts which are positioned on one side of the drape.
Figure 16:
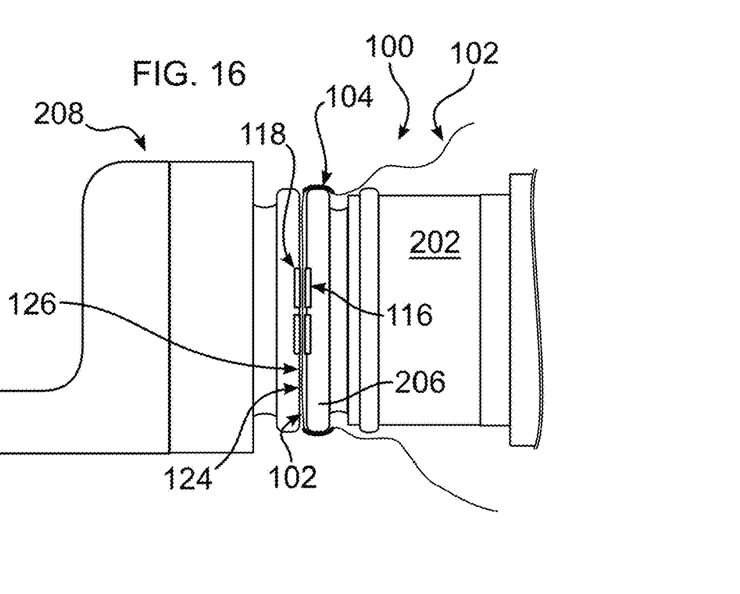
FIG. 16 depicts a tool and an arm of the disclosure, each having an attached mating flange, the tool and arm each having capacitive plates which are disposed on opposite sides of a drape of the disclosure when the flanges are mated and affixed with a clamp.

With reference to FIGS. 13-15, in an alternative embodiment, contact plates 128 are attached to drape 102, and form a direct electrical connection through drape 102 between plates 116 and 118, when clamp 204 is affixed with drape 102 in position over end face 214. As such, induction or conduction is not needed to transfer data or power, although either could still be used by introducing a dielectric gap. In FIG. 13, it may be seen that contact plates 128 can pass through drape 102 and be riveted, for example, to form a sterile barrier. Another type of fastening can be used, such as a threaded fastener or clip. Alternatively, an adhesive or other sealer can be used, or can be used together with another fastener as needed to ensure an adequate seal.

In FIG. 14, contact plates 128 form part of drape 102 and extend from one side surface of drape 102 to the opposite side/surface. For example, a portion of drape can be fabricated with a conductive plastic, or a conductive additive. This portion can be made using 3D printing or can be stamped or welded into place, for example using ultrasonic welding. Contact plates 128 can be positioned to pass through drape 102 and extend above drape 102 (FIG. 13), through drape 102 (FIG. 14), or below drape 102 (FIG. 15).

Still further, a portion of drape 102 can be removed, and a replacement panel 134, indicated for example by a dashed box in FIG. 14, including contact plates 128 can be inserted. Panel 134 can include band 104, or can attach to band 104. Panel 134 can include band 104 and portions interior to band 104, and can include a strain relieving extension to band 104 which extends away from an interior of band 104. Panel 134 can be ultrasonically welded to the remainder of drape 102, or can be bonded in another way, for example adhesive. Panel 134 can include indicia which define a proper orientation of panel 102 for contact alignment, which can be established prior to clamping. Alternatively, if panel 134 includes band 104, indexing to align contacts can be achieved as explained elsewhere herein. In an embodiment, Panel 134 is attached to an intact portion of drape 102, thereby forming a doubled layer within the band portion and extending over end face 214.

In FIG. 15, contacts 128 extend through drape 102 or drape panel 134 to pass an electrical signal through drape 102. However, FIG. 15 can alternatively be considered to depict that drape 102 can be provided with affixed capacitive plates which are positioned on only one side of drape 102. Such capacitive plates could in turn form an electrical connection with contacts 116 (FIG. 13) and pass a signal through drape 102 by capacitive transmission.

Intermediate Coupler

With reference to FIG. 9, in an embodiment of the disclosure, an intermediate coupling 140 is positioned between arm 202 and tool 208. An electrical interface between arm 202 and coupling 208 can be carried out by any method described herein between arm 202 and clamp 204 or tool 208, including capacitive, inductive, or direct electrical connection through drape 102. For example, flange 142 can be considered to replace flange 210, or alternatively, coupling 140 can be affixed to clamp 204, as described elsewhere herein for affixing clamp 204 to tool 208, wherein flange 110/142 is not needed and is absent. As drape 102 passes between coupling 140 and arm 202, no additional draping is needed between coupling 140 and tool 208. As such, direct electrical contacts can be provided between coupling 140 and tool 208. Where clamp 204 is affixed to tool 208, the direct electrical contacts would be formed between coupling 140 and clamp 204, or to a portion of tool 208 which extends through an opening 222 in clamp 204.

Coupling 140 enables tool 208 to be detached or replaced while drape 102 remains clamped to arm 202 and undisturbed. More particularly, a medical practitioner can drape arm 202 as described elsewhere herein and in accordance with applicable health procedures. Drape 102 is pulled taught over end face 214 and otherwise indexed as described herein, and coupling 140 is mated and clamped to flange 206. As noted, this clamped interface is a duplication of the interface between tool 208 and arm 202. Likewise, flange 144 at an opposite end 146 of coupling 140 is a duplication of flange 206, whereby tool 208 can connect to flange 144 as it would have to flange 206, with the distinction that electrical contacts between tool 208 and coupling 140 can be by direct contact.

Intermediate coupling 140 accordingly provides for replacement of tool 208 without a requirement of unclamping drape 102, thereby avoiding an increased likelihood of damage to drape 102. Intermediate coupling can be used with a prior art drape 212 with like benefits.

Power Connector

Figure 17:
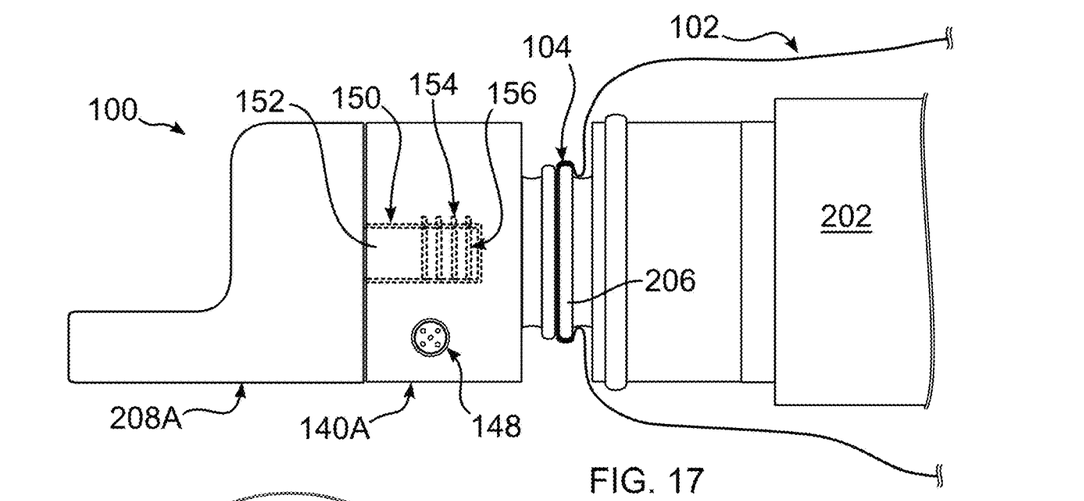
FIG. 17 depicts a tool of the disclosure attached to an intermediate coupling of the disclosure having an electrical socket, the tool have an electrical plug, the intermediate coupling including an outlet socket, and further depicting a drape of the disclosure interposed between an arm and the intermediate coupling.

Tool 208 can at times include a device which uses a substantial amount of power, such as a drill. With reference to FIG. 17, coupling 140 or tool 208 can include output socket 148 which is connected to a power or data signal obtained through the power or data signal passed between connectors or plates 116, 118. By providing output socket 148 upon coupling 140A, accessories can be powered without regards to which tool 208 is currently attached to coupling 140. Output socket 148 is advantageously fabricated using materials and methods which can withstand sterilization by autoclave.

In the embodiment of FIG. 17, it can be seen that an interface between coupling 140A and tool 208A is different than, for example, the interface shown in FIG. 9. More particularly, coupling 140A includes a coupling socket 150, and tool 208A includes a tool plug 152. Coupling socket 150 and tool plug 152 provide for a mechanical coupling of tool 208A and coupling 140A, and can be keyed relative to each other for proper indexing. Electrical contacts 154, 156 are provided upon coupling socket 150 and tool plug 152, respectively, and enable direct transfer of power and data between coupling 140A and tool 208A.

Herein, direct contact connections, whether within a plug and socket disclosed herein or via a direct connection form of plates 116, 118, can have the form of pogo pins, conductive springs or spring loaded plates, or other resilient connection, or any other known or hereinafter developed electrical connection. An advantage of a direct electrical connection is more efficient transfer of energy, and in certain cases increased reliability. Quick release, twist lock, push and pull, or other type of convenient connector styles can be used for plug and socket connections.

In an alternative embodiment, as an alternative or supplement to inductive or capacitive coupling for power as described herein, output socket 148 can function as an input socket, into which a cable carrying power and/or data can be plugged. A cable (not shown) having a plug mateable with socket 148, and which is connectable to a source of power and/or data signal, can be separately sterilized to be present within the sterile field. As such, power can be provided directly to tool 208. Likewise, a data signal can optionally be passed bidirectionally through socket 148.

The disclosure provides a tool 208 coupling method which is more secure and stable in terms of both sterility and the transfer of power and communications. As such, the disclosure enables easier use of the robotics system, particularly in terms of wireless instrumentation, with a consistent power connection, and bidirectional communication which is faster and more robust, while reducing or eliminating drape tearing due to clamping. The electrical connections disclosed herein provide for power transfer and communication which ensure consistent performance during medical procedures, which is critical. Additionally, power capacity for instruments, as well as power transfer efficiency, are increased. Moreover, these advantages are realized while eliminating a requirement for long external power or data cables which could otherwise introduce a trip hazard into the OR.

All references cited herein are expressly incorporated by reference in their entirety. There are many different features of the present disclosure and it is contemplated that these features may be used together or separately. Unless mention was made above to the contrary, it should be noted that all of the accompanying drawings are not to scale. Thus, the disclosure should not be limited to any particular combination of features or to a particular application of the disclosure. Further, it should be understood that variations and modifications within scope of the disclosure might occur to those skilled in the art to which the disclosure pertains. Accordingly, all expedient modifications readily attainable by one versed in the art from the disclosure set forth herein that are within the scope of the present disclosure are to be included as further embodiments of the present disclosure.

What is claimed is:

1. A drape for covering robotic equipment in a medical environment, comprising:
an extended drape portion of a first material sized to cover a robotic arm; and
a shaped drape portion sized to cover an end surface of the robotic arm, the shaped drape portion having a band shaped to correspond to a portion of the robotic arm that is clamped to a tool,
whereby a clamp is configured to pass over the band and clamp the band when the clamp clamps the robotic arm to the tool such that no part of the extended portion is clamped.

2. The drape of claim 1, wherein the shaped drape portion is thicker than the extended drape portion.

3. The drape of claim 1, wherein the shaped drape portion is made of a different type of material than the extended drape portion.

4. The drape of claim 1, wherein the band has at least one indexing region that is shaped to mate with an indexing region of the clamp.

5. The drape of claim 1, wherein the shaped drape portion is made of a dielectric material.

6. The drape of claim 1, wherein the band is a thermoplastic polyurethane.

7. The drape of claim 1, wherein the band includes a first band portion sized to be pressed by the clamp during clamping, and a second band portion extending away from the first portion to thereby provide strain relief at a transition from the shaped drape portion to the extended drape portion.

8. The drape of claim 7, wherein the second band portion is tapered.

9. The drape of claim 1, wherein the shaped drape portion is formed separately from the extended drape portion and affixed to the extended drape portion.

10. The drape of claim 1, wherein the clamp is a v-band type, the robotic arm including a flange squeezed by a v-band of the v-band clamp, the band having a loop shape sized to cover the squeezed portion of the flange.

11. The drape of claim 1, wherein the robotic arm includes a flange squeezed by the clamp, wherein the flange comprises the band and the band has a loop shape sized to cover the squeezed portion of the flange.

12. The drape of claim 1, wherein the shaped drape portion includes a plurality of electrically conductive contacts, and wherein the electrically conductive contacts conduct electricity from a first side of the shaped drape portion to a second side of the shaped drape portion opposite to the first side.

13. The drape of claim 12, wherein the electrically conductive contacts are integrally formed within the shaped drape portion by 3D printing.

14. The drape of claim 1, wherein a plurality of capacitive plates are affixed to, positioned within, and on a first side of the shaped drape portion.

15. The drape of claim 1, wherein the shaped drape portion includes electrically conductive contacts.

16. A drape for covering robotic equipment in a medical environment, comprising:
an extended drape portion of a first material sized to cover a robotic arm; and
a shaped drape portion sized to cover an end surface of the robotic arm, the shaped drape portion having a band shaped to correspond to a flange of the robotic arm and having an indexing shape which corresponds to an indexing shape of the flange,
whereby a clamp is configured to pass over the band and clamp the band when the clamp clamps the arm portion to a tool such that no part of the extended drape portion is clamped.

17. The drape of claim 16, wherein the shaped drape portion includes a plurality of electrically conductive contacts, and wherein the electrically conductive contacts conduct electricity from a first side of the shaped drape portion to a second side of the shaped drape portion opposite to the first side.

18. The drape of claim 17, wherein the electrically conductive contacts are integrally formed within the shaped drape portion by 3D printing.

19. The drape of claim 16, wherein a plurality of capacitive plates are affixed to, positioned within, and on a first side of the shaped drape portion.

20. The drape of claim 16, wherein the shaped drape portion includes electrically conductive contacts.

* * * * *